United States Patent
von Haken Spence et al.

[11] Patent Number: 6,051,667
[45] Date of Patent: Apr. 18, 2000

[54] OLEFIN POLYMERIZATION USING A CATALYST HAVING A BRIDGED CYCLOPENTADIENYL-PHOSPHOLE LIGAND

[75] Inventors: Rupert Edward von Haken Spence; Xiaoliang Gao; Linda Koch; Stephen John Brown; Daryll G. Harrison; Qinyan Wang, all of Calgary, Canada

[73] Assignee: Nova Chemicals (International) S.A., Villars-sur-Glane, Switzerland

[21] Appl. No.: 09/065,594

[22] Filed: Apr. 24, 1998

[30] Foreign Application Priority Data

May 8, 1997 [CA] Canada ................................ 2204803

[51] Int. Cl.[7] ...................................................... C08F 4/44
[52] U.S. Cl. ........................ 526/127; 526/160; 526/161; 526/172; 526/943; 502/155
[58] Field of Search ................... 526/160, 161, 526/172, 943, 127; 502/155

[56] References Cited

U.S. PATENT DOCUMENTS

| | | | |
|---|---|---|---|
| 5,153,157 | 10/1992 | Hlatky et al. | 502/117 |
| 5,198,401 | 3/1993 | Turner et al. | 502/155 |
| 5,324,800 | 6/1994 | Welborn, Jr. et al. | 526/160 |
| 5,387,568 | 2/1995 | Ewen et al. | 502/104 |
| 5,434,116 | 7/1995 | Sone et al. | 502/103 |
| 5,554,795 | 9/1996 | Frey et al. | 568/8 |
| 5,563,284 | 10/1996 | Frey et al. | 556/53 |
| 5,565,396 | 10/1996 | Frey et al. | 502/113 |
| 5,756,417 | 5/1998 | De Boer et al. | 502/117 |

FOREIGN PATENT DOCUMENTS

| | | |
|---|---|---|
| 0617052A2 | 9/1994 | European Pat. Off. . |
| 0741145A1 | 11/1996 | European Pat. Off. . |
| WO 95/04087 | 2/1995 | WIPO . |

*Primary Examiner*—David W. Wu
*Assistant Examiner*—Roberto Rabago
*Attorney, Agent, or Firm*—Kenneth H. Johnson

[57] ABSTRACT

An olefin polymerization process uses a catalyst with an organometallic complex of a group 4 metal having a bridged cyclopentadienyl-phosphole ligand, as defined by the formula:

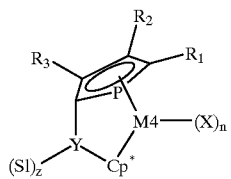

wherein:
  each Sl is a non-interfering spectator ligand;
  Y is selected from Si, Ge and Sn;
  Z is 2;
  $R_1$, $R_2$, and $R_3$ are hydrogen or non-interfering substituents;
  Cp* is selected from cyclopentadienyl, substituted cyclopentadienyl, indenyl, substituted indenyl, fluorenyl and substituted fluorenyl;
  M4 is selected from Ti, Zr and Hf;
  X is an anionic ligand; and
  n is 1 or 2, depending upon the oxidation state of M4.

A catalyst having a fluorenyl ligand and a dimethyl silyl bridge is preferred. This invention may be used to prepare polyethylenes having a broad molecular weight distribution.

14 Claims, No Drawings

OLEFIN POLYMERIZATION USING A CATALYST HAVING A BRIDGED CYCLOPENTADIENYL-PHOSPHOLE LIGAND

FIELD OF THE INVENTION

This invention relates to a new family of phospholes and a process to prepare these phospholes; to a process to use these phospholes to prepare a family of organometallic compounds having a cyclopentadienyl-type ligand which is bridged through a metalloid to a phospholyl ligand ("Cp-bridged-phosphole") and to a process to polymerize olefins using a Cp-bridged-phosphole.

BACKGROUND OF THE INVENTION

Cyclopentadienyl-type ligands have been used to prepare organometallic complexes which, in turn, are useful in such applications as olefin polymerizations, alkene isomerizations and hydrogenations.

More recently, the use of phospholes to prepare phospholyl-type organometallic complexes has been disclosed.

The use of phospholyl-type complexes (and "mixed" cyclopentadienyl/phospholyl complexes—i.e. a complex having a cyclopentadienyl and a phospholyl-type ligand) is disclosed in U.S. Pat. No. 5,434,116 (Sone, to Tosoh), published European Patent Office (EPO) applications 617,052 (Aoki et al, to Asahi), and EPO 741,145 (Katayama et al, to Sumitomo) and Patent Cooperation Treaty (PCT) application 95/04087 (de Boer et al, to Shell).

It is also known to prepare "bridged and substituted" cyclopentadienyl-type ligands—as disclosed, for example, in U.S. Pat. Nos. 5,563,284; 5,565,396, and 5,554,795 (Frey et al), U.S. Pat. No. 5,324,800 (Welborn). These "bridged" cyclopentadienyls form catalyst systems for olefin polymerization when activated by a "substantially non-coordinating anion" (as disclosed by Hlatky and Turner in U.S. Pat. Nos. 5,153,157 and 5,198,401) or an alumoxane.

However, there is no known teaching of any process to prepare ligands having a cyclopentadiene-type group which is bridged to a phosphole.

SUMMARY OF THE INVENTION

An object of the present invention is to provide a new family of phospholes and a process to prepare the phospholes.

Another object of the invention is to use the new phospholes to prepare a family of new organometallic complexes having a bridged ligand with a metalloid "bridge" between a cyclopentadienyl group and a phospholyl group.

Another object of the invention is to provide processes for olefin polymerization using a catalyst system which includes these new organometallic complexes and an activator.

Thus, in one embodiment of the invention there is provided a phosphole characterized by having at least two substituents (a) and (b) where substituent (a) is a leaving group bonded to the phosphorus atom in the phosphole ring and substituent (b) is bonded to one carbon atom in the phosphole ring and is defined by the formula:

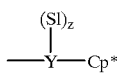

wherein Cp* is selected from cyclopentadienyl; substituted cyclopentadienyl; indenyl; substituted indenyl; fluorenyl and substituted fluorenyl; each Sl is a non-interfering spectator ligand; Y is a metalloid bridging atom selected from Si, Ge, Sn, N, P, B and Al; and Z is one, two or three depending upon the valence of atom Y. For example, if Y is Si or Ge (which are four valent), then Z is 2. Similarly, if Y is three valent nitrogen, then Z is 1.

In another embodiment, this invention provides a process to prepare a phosphole as described above wherein the process comprises the reaction of a reactive organometallic cyclopentadienyl reagent with a halogenated phosphole defined by the formula:

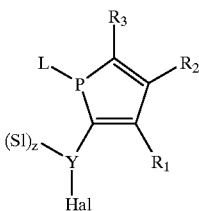

wherein:

$R_1$, $R_2$, and $R_3$, are hydrogen or non-interfering substituents;

Sl is a spectator ligand;

Y is Si, Ge, Sn, N, P, B and Al;

Z is one, two or three depending upon the valence of Y;

L is a leaving group; and

Hal is a halogen or pseudohalogen.

In another embodiment, the invention provides a process to prepare group 4 metal complexes of the above-described phospholes.

In another embodiment, the invention provides a process for polymerizing at least one polymerizable alpha olefin comprising reacting an activator and a group 4 organometallic complex of the present, inventive phospholes.

In a preferred embodiment, there is provided a high temperature olefin polymerization process using an activator and catalyst in which the catalyst is a group 4 organometallic complex defined by the formula:

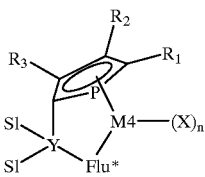

wherein:

Flu* is selected from fluorenyl and substituted fluorenyl;

each Sl is a non-interfering spectator ligand;

Y is selected from Si, Ge, and Sn;

$R_1$, $R_2$, and $R_3$ are hydrogen or non-interfering substituents;

M4 is selected from Ti, Zr and Hf; and each X is an anionic ligand and n is 1 or 2 depending upon the oxidation state of M4.

DETAILED DESCRIPTION

PART I

Novel Phospholes

The novel phospholes of the present invention are characterized by having (a) a substituent which is a leaving group (to facilitate further manipulations of the phosphole molecule); and (b) a substituent which includes a cyclopentadienyl structure and a metalloid bridge between the phosphole and the cyclopentadienyl structure.

A discussion of each of the features of these novel phospholes is provided below.

The term "phosphole" is meant to convey its conventional meaning, namely a cyclic dienyl structure having four carbon atoms and one phosphorus atom in the ring. The simplest phosphole is illustrated below:

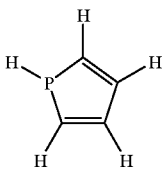

It will be readily appreciated by those skilled in the art that the hydrogen atoms shown in the above formula may be replaced with other substituents.

The novel phospholes of this invention contain a cyclopentadiene-type group. As used herein the term "cyclopentadiene-type" is meant to convey its conventional meaning and to include indene and fluorene ligands. The simplest (unsubstituted) cyclopentadiene, indene and fluorene structures are illustrated below.

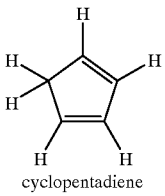
cyclopentadiene

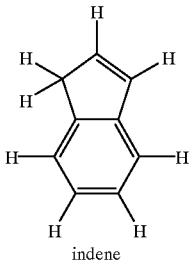
indene

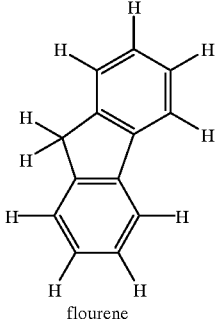
flourene

It will be readily appreciated by those skilled in the art that the hydrogen atoms shown in the above formula may be replaced with substituents to provide the "substituted" analogues. Thus, in the broadest sense, the inventive phospholes contain a cyclopentadienyl structure which may be an unsubstituted cyclopentadienyl, unsubstituted indenyl, substituted indenyl, unsubstituted fluorenyl or substituted fluorenyl. A description of permissible substituents on these cyclopentadienyl type structures is provided in the aforementioned Welborn '800 reference.

An illustrative list of such substituents for cyclopentadienyl groups includes $C_1$–$C_{20}$ hydrocarbyl radicals; substituted $C_1$–$C_{20}$ hydrocarbyl radicals wherein one or more hydrogen atoms is replaced by a halogen radical, an amido radical, a phosphido radical, an alkoxy radical or a radical containing a Lewis acidic or basic functionality; substituted $C_1$–$C_{20}$ hydrocarbyl radicals wherein the substituent contains an atom selected from the group 14 of the Periodic Table of Elements (where group 14 refers to IUPAC nomenclature); and halogen radicals, amido radicals, phosphido radicals, alkoxy radicals, alkyborido radicals, or a radical containing Lewis acidic or basic functionality; or a ring in which two adjacent R-groups are joined forming $C_1$–$C_{20}$ ring to give a saturated or unsaturated polycyclic ligand.

It should be further noted that the aforementioned Frey et al references teach cyclopentadienyl type ligands (including indenyl and fluorenyl) which may be substituted with phosphorus-containing substituents. By way of clarification, the phosphorus-containing substituents disclosed by Frey et al are not within a ring structure (i.e. Frey et al do not disclose phospholes but, rather, phosphido or phosphino substituted cyclopentadienyls).

The inventive phospholes contain a metalloid bridge between the phosphole ring and the cyclopentadienyl structure. The term "metalloid" as used herein is meant to refer to the group which includes silicon (Si); germanium (Ge); Tin (Sn); nitrogen (N); phosphorus (P); boron (B); and aluminum (Al). The "metalloid" is a "bridging" atom which is bonded to a carbon atom in the phosphole ring and to the cyclopentadienyl group. The metalloid has additional valences which are filled with "spectator" ligands (i.e. ligands which must be on the metalloid but which are not important to the substance of this invention). Illustrative examples of spectator ligands include hydrogen, halides, and hydrocarbyl ligands containing from 1 to 15 carbon atoms. For convenience, it is preferred that each of the spectator ligands is either a —$CH_3$ (methyl) fragment or phenyl fragment.

The preferred metalloids are Si, Ge, and Sn with Si being especially preferred. Thus, the preferred phospholes are illustrated by the formula:

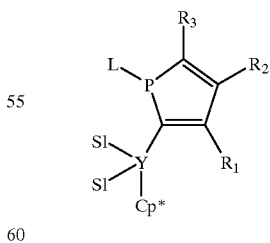

wherein:

$R_1$, $R_2$, and $R_3$ are hydrogen or non-interfering substituents;

Y is Si, Ge or Sn;

Sl is a spectator ligand;

L is a leaving group; and

Cp* is a cyclopentadienyl-type structure as described above.

As shown in the above formula, it is most preferred that the metalloid is bonded to a carbon atom adjacent to the phosphorus atom of the phosphole.

The (optional) "non-interfering" substituents on the phosphole (i.e. $R_1$, $R_2$, and $R_3$) generally encompass any substituent which doesn't interfere with further manipulation of the phosphole. An illustrative list of non-interfering substituents includes $C_1$–$C_{20}$ hydrocarbyl radicals; substituted $C_1$–$C_{20}$ hydrocarbyl radicals wherein one or more hydrogen atoms is replaced by a halogen radical, an amido radical, a phosphido radical, an alkoxy radical or a radical containing a Lewis acidic or basic functionality; substituted $C_1$–$C_{20}$ hydrocarbyl radicals wherein the substituent contains an atom selected from the group 14 of the Periodic Table of Elements; and halogen radicals, amido radicals, phosphido radicals, alkoxy radicals, alkyborido radicals, or a radical containing Lewis acidic or basic functionality; or a ring in which two adjacent R-groups are joined forming $C_1$–$C_{20}$ ring to give a saturated or unsaturated polycyclic ligand.

The inventive phospholes are further characterized by having a "leaving group" bonded to the phosphorus atom in the ring.

As used herein, the term "leaving group" is intended to convey its conventional meaning to organometallic chemists—i.e. a fragment or group which may be cleaved off in a manner which facilitates further manipulation of the subject molecule. Examples of suitable leaving groups bonded to the phosphorus atom include a single H atom (which may, for example, be cleaved off with an alkyl lithium reagent), trialkyl (or triaryl) tin, trialkyl (or triaryl) Si; group 1 or group 2 atoms, or aryl, with aryl (especially phenyl) being preferred.

The inventive phospholes may be used to prepare organometallic complexes, such as Group 4 metal complexes having a dianonic ligand with a metalloid bridge, a phospholyl ligand group which is pi bonded to the metal and cyclopentadienyl-ligand group which is also pi bonded to the metal.

PART II
Process to Prepare the Phospholes

The preferred process to prepare the novel phospholes is by reacting an organometallic cyclopentadienyl reagent and a "bifunctional phosphole".

The organometallic cyclopentadienyl reagent is defined by the formula:

Cp*M wherein Cp* is selected from unsubstituted cyclopentadienyl, substituted cyclopentadienyl, unsubstituted indenyl, substituted indenyl, unsubstituted fluorenyl, and substituted fluorenyl; and M is a group 1 or 2 metal (i.e. Li, Na, K, Rb, Cs, Be, Mg, Ca, Sr or Ba) or Al or Tl.

The "bifunctional phosphole" has (a) a leaving group bonded to the phosphorus atom and (b) a halogen or pseudohalogen containing group bonded to a carbon atom adjacent to the phosphorus atom. The preparation of such a bifunctional phosphole is described in the examples.

The term "leaving group" is used in the manner previously discussed (with the preferred leaving group being aryl, especially phenyl).

The term halogen is well known and the term pseudohalogen is also used conventionally—i.e. to identify (to a skilled organometallic chemist) a group which will behave similarly to a halogen in subsequent manipulations of the molecule. A common pseudohalogen is an —OR group (where the R is hydrogen or a hydrocarbyl fragment having from 1 to 20 carbon atoms).

The preferred group of organometallic reagents are Li salts of substituted fluorenyls.

The reaction preferably is undertaken in a solvent (or diluent) such as an ether, a $C_{5-20}$ alkane, an aromatic or mixture thereof at a temperature of from −100° C. to 150° C. (most preferably from −78° C. to 25° C.).

PART III
Preparation of Group 4 Organometallic Complexes

The preferred process to prepare the group 4 organometallic complexes is undertaken by reacting a group 4 metal (i.e. Ti, Hf or Zr) complex with a reagent derived from the novel phosphole complexes described in Part I above.

The group 4 metal is preferably in the highest oxidation state (though Ti(III) is also suitable) and is most preferably a tetrahalide (especially $ZrCl_4$).

The preferred initial step is to lithiate the phosphole. In some instances it may be possible to obtain the desired group 4 organometallic complexes from a direct reaction between the lithiated phosphole and the metal halide. However, in other instances it may be necessary to prepare an intermediate reagent (for example, by reaction of the lithiated phosphole with trimethyl silicon chloride or trimethyl tin chloride, and then reacting this intermediate with the group 4 metal halide—as illustrated in the Examples). (Skilled organometallic chemists will recognize that the use of this intermediate involves extra time/expense but can improve the final yield of the group 4 organometallic complex.)

The reaction preferably is done in a solvent (or diluent) such as an ether, alkane, or aromatic. Toluene is the most preferred solvent.

The reaction temperature is preferably from −150° C. to 250° C. (most preferably from 20° C. to 150° C.).

The resulting group 4 organometallic complexes are defined by the following formula ("formula 1"):

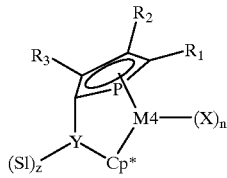

wherein:

$R_1$, $R_2$, and $R_3$ are hydrogen or non-interfering substituents (as described in Part I above);

is a metalloid bridge having at least one spectator ligand (as described in Part 1 above);

Cp* is a cyclopentadienyl, indenyl or fluorenyl (each optionally substituted as described in Part 1 above);

M4 is a group 4 metal (i.e. Ti, Zr or Hf); and

X is a ligand or ligands bonded to the group 4 metal and n is 1 or 2 depending upon the oxidation state of M4.

By way of further explanation: If the group 4 metal is in oxidation state +3 and X is a simple anionic ligand then there will be only one X (and similarly, there will be two X ligands if the metal is 4+). X is, in general, a simple anionic ligand.

Any such simple anionic ligand which may be bonded to an analogous metallocene complex should be acceptable in the present complexes. An illustrative list of such anionic ligands includes hydrogen, amidos, halogens and hydrocarbyls having up to 10 carbon atoms (with chlorine being preferred, for simplicity).

PART IV

Polymerization

The polymerization process of this invention is conducted in the presence of a catalyst which is an organometallic complex according to the aforedefined formula 1 and an "activator or cocatalyst". The terms "activator" or "cocatalyst" may be used interchangeably and refer to a catalyst component which combines with the organometallic complex to form a catalyst system that is active for olefin polymerization.

Preferred cocatalysts are the well known alumoxane (also known as aluminoxane) and ionic activators.

The term "alumoxane" refers to a well known article of commerce which is typically represented by the following formula:

where each R' is independently selected from alkyl, cycloalkyl, aryl or alkyl substituted aryl and has from 1–20 carbon atoms and where m is from 0 to about 50 (especially from 10 to 40). The preferred alumoxane is methylalumoxane or "MAO" (where each of the R' is methyl).

Alumoxanes are typically used in substantial molar excess compared to the amount of metal in the catalyst. Aluminum:transition metal molar ratios of from 10:1 to 10,000:1 are preferred, especially from 50:1 to 500:1.

As used herein, the term "ionic activator" is meant to refer to the well known cocatalyst systems described in the aforementioned Hlatky and Turner U.S. patent references, and the carbonium, sulfonium and oxonium analogues of such ionic activators which are disclosed by Ewen in U.S. Pat. No. 5,387,568. In general, these ionic activators form an anion which only weakly coordinates to a cationic form of the catalyst. Such "ionic cocatalysts" may or may not contain an active proton (e.g. trimethyl ammonium, tributylammonium; N,N-dimethyl anilinium, carbonium, oxonium or sulfonium). They do contain a labile substantially non-coordinating anion (such as tetraphenyl borate or tetrakis(pentafluorophenyl) borate). The preferred of these ionic activators are tris(pentafluorophenyl) borane (which can generate the borate upon reaction with the organometallic catalyst complex), [triphenyl methyl][tetrakis (pentafluorophenyl) borate] and [N,N-dimethyl anilinium] [tetrakis(pentafluorophenyl) borate]. In commercial practice, the triphenyl methyl (or "carbonium") salts may be preferred.

These ionic activators are typically used in approximately equimolar amounts (based on the transition metal in the catalyst) but lower levels may also be successful and higher levels also generally work (though sub-optimally with respect to the cost-effective use of the expensive activator).

In addition to the catalyst and cocatalyst, the use of a "poison scavenger" may also be desirable. As may be inferred from the name "poison scavenger", these additives may be used in small amounts to scavenge impurities in the polymerization environment. Aluminum alkyls, for example triisobutyl aluminum, are suitable poison scavengers. (Note: some caution must be exercised when using poison scavengers as they may also react with, and deactivate, the catalyst.)

Polymerizations according to this invention may be undertaken in any of the well known olefin polymerization processes including those known as "gas phase", "slurry", "high pressure" and "solution".

The use of a supported catalyst is preferred for gas phase and slurry processes whereas a non-supported catalyst is preferred for the other two.

When utilizing a supported catalyst, it may be preferable to initially support the cocatalyst, then the catalyst (as will be illustrated in the Examples).

The polymerization process according to this invention uses at least one olefin monomer (such as ethylene, propylene, butene, hexene) and may include other monomers which are copolymerizable therewith (such as other alpha olefins, preferably butene, hexene or octene, and under certain conditions, dienes such as hexadiene isomers, vinyl aromatic monomers such as styrene or cyclic olefin monomers such as norbornene).

It is especially preferred that the polymerization process utilize a major portion of ethylene monomer and a minor portion of an alpha olefin comonomer selected from butene, hexene and octene so as to produce a linear low density polyethylene ("LLDPE") product.

Our experimental data illustrate that organometallic complexes prepared from phospholes according to this invention are excellent polymerization processes. The organometallic complexes having a bridged fluorenyl phospholyl ligand according to this invention display particularly desirable behavior in high temperature ethylene polymerization in that the resulting polyethylene has high molecular weight.

The most preferred polymerization process of this invention encompasses the use of the novel catalysts (together with a cocatalyst) in a medium pressure solution process. As used herein, the term "medium pressure solution process" refers to a polymerization carried out in a solvent for the polymer at an operating temperature from 100 to 320° C. (especially from 120 to 220° C.) and a total pressure of from 3 to 35 mega Pascals. Hydrogen may be used in this process to control (reduce) molecular weight. Optimal catalyst and cocatalyst concentrations are affected by such variables as temperature and monomer concentration but may be quickly optimized by non-inventive tests.

Further details concerning the medium pressure polymerization process (and the alternative gas phase, slurry and high pressure processes) are well known to those skilled in the art (and widely described in the open and patent literature).

EXAMPLES

The invention will now be illustrated in further detail by way of the following non-limiting examples. For clarity, the Examples have been divided into three parts, namely Part A (Synthetic Methods), Part B (Solution Polymerization), and Part C (Gas Phase Polymerization).

PART A

Synthetic Methods

Part A is divided into five sub-sections: Part A1 (Synthesis of a novel phosphole, namely 2-(cyclopentadienyldimethylsilyl)-1-phenyl-3,4,5-trimethylphosphole); Part A2 (Synthesis of ansa-[dimethylsilyl($\eta^5$-cyclopentadienyl-3,4,5-trimethylphospholyl] zirconium dichloride—also referred to herein as Me$_2$Si(Cp)(C$_4$PMe$_3$)ZrCl$_2$); Part A3 (Synthesis of ansa-[dimethylsilyl($\eta^5$-fluorenyl)($\eta^5$-3,4,5-trimethylphospholyl)] zirconium dichloride—also referred to herein as Me$_2$Si(Flu)(C$_4$PMe$_3$)ZrCl$_2$); Part A4 (Synthesis of ansa-[dimethylsilyl($\eta^5$-fluorenyl)($\eta^5$-3,4-dimethylphospholyl)] zirconium dichloride—also referred to herein as Me$_2$Si(Flu)(C$_4$PHMe$_2$)ZrCl$_2$); and Part A5 (Synthesis of 2-dimethyl(2,7-di-tert-butyl-9-fluorenyl)silyl-3,4,5-trimethyl-1-phenylphosphole).

PART A1

Synthesis of 2-(cyclopentadienyldimethylsilyl)-1-phenyl-3,4,5-trimethylphosphole)

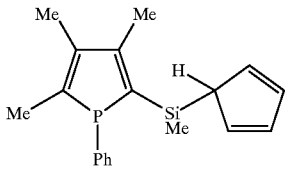

Step 1. Preparation of Chlorodimethyl-1-propynylsilane

To a solution of dichlorodimethylsilane (60 milliliters (mL), 495 millimoles (mmol)) in diethyl ether (75 mL) at −20° C. was added a tetrahydrofuran (THF) solution of propynylmagnesium bromide (200 mL, 0.5 molar (M), 100 mmol). Addition was completed over 30 minutes and then the reaction was allowed to warm to room temperature. The solvent and excess silane were distilled off at ambient pressure and the residue filtered to remove solids. The resulting oil was distilled at ambient pressure and the fraction boiling between 90–120° C. was isolated. Redistillation gave pure product. Yield, 4.654 grams (g). Proton nuclear magnetic resonance spectrum ($^1$H NMR) in deuterated toluene (C$_7$D$_8$): 1.38 (peak area=3 protons (3H)), 0.391(6H).

Step 2. Preparation of bis($\eta$5-cyclopentadien-1-yl)(1-chlorodimethylsilyl-2,3,4-trimethyl-1,3-butadienyl-1,4-diyl) zirconium To a slurry of bis(cyclopentadienyl)zirconium chloride hydride (3.802 g, 14.74 mmol) in methylene chloride (50 mL) at 0° C. was added 2-butyne (2.5 mL, 1.72 g, 32 mmol). The reaction was allowed to warm to room temperature and after 30 minutes a clear solution had formed. The solvent and excess butyne were removed in vacuo and the residues dissolved in THF (30 mL). The solution was cooled to −78° C. and a solution of methyl lithium in ether (1.4M, 10.5 mL, 15 mmol) was added. After 15 minutes chlorodimethyl-1-propynylsilane (1.955 g, 14.7 mmol) was added and the reaction mixture allowed to warm to room temperature. During warming gas evolution was apparent. The reaction was stirred at room temperature for 45 minutes, at 45° C. for 2 hours and then at room temperature overnight. The solvent was removed in vacuo and the residues treated with hexane (50 mL). The reaction was filtered and the filtrate concentrated until crystals started to form. The reaction was then stored at −15° C. for two days. The mother liquor was cannulated away and the orange crystals dried in vacuo. Yield, 4.2 g. $^1$H NMR (C$_7$D$_8$): 6.01 (10H), 1.78 (3H), 1.65 (3H), 1.53 (3H), 0.50 (6H).

Step 3. Preparation of 2-chlorodimethylsilyl-1-phenyl-3,4,5-trimethylphosphole

Bis($\eta$5-cyclopentadien-1-yl)(1-chlorodimethylsilyl-2,3,4-trimethyl-1,3-butadienyl-1,4-diyl) zirconium (2.11 g, 5.18 mmol) and phenylphosphine dichloride (0.926 g, 5.18 mmol) were combined with toluene (40 mL) and heated to reflux for three hours. The reaction was allowed to cool to room temperature and the solvent was removed in vacuo. Hexane (50 mL) was added and the reaction mixture cooled to 0° C. Subsequent filtration and removal of the solvent yielded a dark orange oil. This was further purified by a second hexane extraction to remove zirconocene dichloride. Yield, 1.358 g. $^1$H NMR (C$_7$D$_8$): 7.27 (multiplet (m), 2H), 7.00 (m, 3H), 2.17 (doublet (d), coupling constant (J)=4.4 Hz, 3H), 1.81 (d, J=11.6 Hz, 3H), 1.66 (3H), 0.46 (3H), 0.41 (3H).

Step 4. Preparation of 2-(cyclopentadienyldimethylsilyl)-1-phenyl-3,4,5-trimethylphosphole To a solution of 2-chlorodimethylsilyl-1-phenyl-3,4,5-trimethylphosphole (552 mg, 1.87 mmol) in THF (15 mL) at −78° C. was added a THF (20 ml) solution of CpLi (136 mg). The solution became cloudy and was allowed to warm to room temperature. The reaction was stirred overnight and then the solvent was removed in vacuo and the product characterized by 1H NMR spectroscopy. The NMR spectrum showed the product was form in high yield with good purity. $^1$H NMR (C$_7$D$_8$): 7.3, 7.0, 6.7 (broad), 2.07 (d), 1.85 (d), 1.74, 0.12, −0.04.

Note

One might briefly summarize the above described synthesis of "bridged phosphole" structures as involving the crucial steps of (a) reacting the zirconacycle with a phosphine dihalide (Step 3 of Part A1) followed by (b) reacting the phosphole product from (a) with an organometallic cyclopentadienyl reagent (Step 4 of Part A1). It will be appreciated by those skilled in the art that the reverse order of steps (a) and (b) may also be used to access the inventive phospholes from the zirconacycle (i.e. first react the zirconacycle with the organometallic cyclopentadienyl reagent, then react the resulting intermediate with a phosphine dihalide). Similarly, it will be further recognized that the inventive phospholes may also be accessed from the 2-halophosphole via metallation and treatment with a cyclopentadienyl substituted silane which is functionalized with a leaving group (e.g. Cp-SiMe$_2$Cl). (A discussion of the preparation of a 2-halophosphole is provided in Part A4 below.)

PART A2

Synthesis of ansa-[dimethylsilyl($\eta^5$-cyclopentadienyl)($\eta^5$-3,4,5-trimethylphospholyl] zirconium dichloride

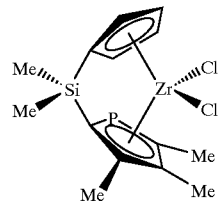

A solution of 2-(cyclopentadienyldimethylsilyl)-1-phenyl-3,4,5-trimethylphosphole (1.87 mmol, from the previous experiment) in THF (20 mL) was added to lithium foil (37 mg). After being stirred for 2.5 hours, the dark red solution was added to a solution of trimethyltin chloride (870 mg, 4.37 mmol) in THF (10 mL) at −78° C. The reaction was warmed to room temperature and stirred for one hour. The resulting pale orange solution was then added to ZrCl$_4$.2THF (705 mg, 1.87 mmol) in THF (10 mL) at −78° C. The reaction was stirred overnight at room temperature before the THF and other volatiles were removed in vacuo and toluene added. The toluene solution was heated to 100° C. for 1.5 hours, filtered and the volatiles were removed in vacuo. Pure product was obtained by recrystallizing the resulting residue from toluene and hexane at −30° C. Yield, 138 mg of high purity product plus 369 mg of >90% purity product. $^1$H NMR (C$_7$D$_8$): 6.79 (1H), 6.63 (1H), 5.90 (1H), 5.39 (1H), 2.23 (d, J=10.3 Hz, 3H), 1.97 (3H), 1.71 (3H), 0.54 (3H), 0.29 (3H).

PART A3

Synthesis of Ansa-[dimethylsilyl(η$^5$-fluorenyl)(η$^5$-3,4,5-trimethylphospholyl)] Zirconium Dichloride

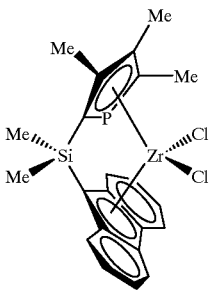

Step 1. Preparation of 2-dimethyl(9-fluorenyl)silyl-1-phenyl-3,4,5-trimethylphosphole

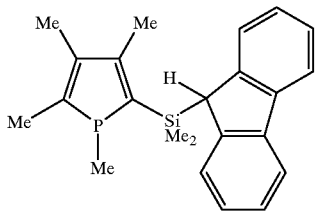

To a solution of 2-chlorodimethylsilyl-1-phenyl-3,4,5-trimethylphosphole (0.496 g, 1.68 mmol) in THF (15 mL) at −78° C. was added a THF (15 mL) solution of fluorenyl lithium (0.294 mg, 1.70 mmol). The reaction was warmed to room temperature and stirred for 2 hours. Removal of the solvent gave the product. $^1$H NMR (C$_7$D$_8$): 7.7 (d), 7.4 (m), 7.2 (m), 6.9 (m), 3.95 (s), 2.02 (d), 1.87 (d), 1.8 (s), 0.12 (s), −0.30 (s).

Step 2. Preparation of ansa-[dimethylsilyl(η$^5$-fluorenyl)(η$^5$-3,4,5-trimethylphospholyl)] zirconium dichloride A solution of 2-dimethyl(9-fluorenyl)silyl-1-phenyl-3,4,5-trimethylphosphole (1.65 mmol) in THF (30 mL) was added to lithium foil (33 mg, 4.7 mmol) at room temperature. Over the next two hours the reaction became a deep red color. The solution was cannulated away from the excess lithium and added to a solution of trimethyltin chloride (750 mg, 3.8 mmol) in THF (15 mL) at −78° C. The reaction was allowed to warm to room temperature and it became almost colorless. [A small aliquot of this reaction mixture was taken and examined by $^1$H NMR spectroscopy. The NMR spectrum showed that the distannyl had form essentially quantitatively. $^1$H NMR (C$_7$D$_8$): 7.85, 7.55, 7.2, 1.95 (d), 1.66 (s), 1.36(s), 0.55 (s), 0.15 (d), −0.11 (s).] The THF and other volatiles were removed in vacuo from the reaction mixture and the residue dissolved in toluene (15 mL). The reaction mixture was then added to a toluene (15 mL) slurry of ZrCl$_4$ at −78° C. After warming to room temperature the reaction was heated to 100° C. for 5 hours and then filtered hot. The residues were washed with hot toluene and the toluene fractions combined. Concentration of the orange toluene solution to 50 mL and cooling to −15° C. overnight gave deep orange crystals of the product. $^1$H NMR (C$_7$D$_8$): 7.9–7 (m), 2.0 (d, 3H), 1.9 (d, 6H), 0.92 (3H), 0.88 (3H).

PART A4

Synthesis of ansa-[dimethylsilyl(η$^5$-fluorenyl)(η$^5$-3,4-dimethylphospholyl)] zirconium dichloride

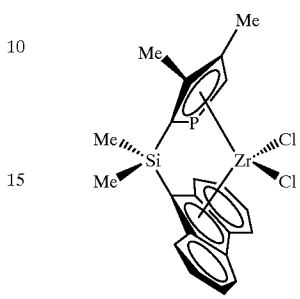

Step 1. 2-Bromo-3,4-diemthyl-1-phenylphosphole was prepared according to a literature method (E. Deschamps and F. Mathey, Bull. Soc. Chim. Fr. 1992, 129, 486.).

Step 2. Preparation of 2-chlorodimethylsilyl-3,4-dimethyl-1-phenylphosphole $^n$BuLi ((1.6 M, 2.33 mL, 3.74 mmol) was added dropwise to a solution of 2-bromo-3,4-dimethyl-1-phenylphosphole (1.0 g, 3.74 mmol) in THF (15 mL) at −105° C. The resultant orange solution was stirred at −100° C. for 45 min to ensure complete lithiation. Me$_2$SiCl$_2$ (4.82 g, 37.4 mmol) was then added. The solution was stirred for 12 hr while the reaction was warmed to 23° C. The solution was pumped to dryness and the residue was extracted with hexane. The hexane extract was pumped to dryness to give the product as an almost colorless oil in quantitative yield. $^1$H NMR (C$_7$D$_8$): 0.42 (s, 6H), 2.127(dd, J$_1$=2.91 Hz, J$_2$=1.34 Hz, 3H), 2.32 (d, J=4.4 Hz, 3H), 6.75 (d, J=40 Hz, 1H), 7.2–7.4 (m, 5H).

Step 3. Preparation of 2-dimethyl(9-fluorenyl)silyl-3,4-dimethyl-1-phenylphosphole

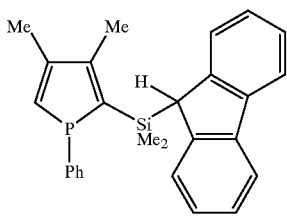

A solution of 2-chlorodimethylsilyl-3,4-dimethyl-1-phenylphosphole (3.74 mmol) in THF (20 mL) was cooled to −100° C. Fluorenyl lithium (0.643 g, 3.74 mmol) in THF(20 mL) was then added. The resultant mixture was stirred for 4 hr while it warmed to 23° C. and then it was heated to 50° C. for 20 min. The solution was pumped to dryness and the residue was dissolved in toluene (10 mL). The toluene solution was passed through a short column of neutral alumina (Brockman activity 1). The column was thoroughly rinsed with toluene to ensure all the desired product was freed from the column. The combined filtrate was pumped to dryness to give the product. Yield 1.435 g, 3.495 mmol, 94%. $^1$H NMR (C$_7$D$_8$): −0.3 (br. s, 3H), 0.15 (br. s, 3H), 1.95 (dd, J$_1$=3.0 Hz, J$_2$=1.4 Hz, 3H), 2.01 (dd, J$_1$=4.5 Hz, J$_2$=1.0 Hz, 3H), 3.93 (s, 1H), 6.70 (d, J=41 Hz, 1H), 6.9–7.8 (m, 13H).

Step 4. Preparation of ansa-[dimethylsilyl($\eta^5$-fluorenyl)($\eta^5$-3,4-dimethylphospholyl)]zirconium dichloride 2-dimethyl(9-fluorenyl)silyl-3,4-dimethyl-1-phenylphosphole (0.717 g, 1.747 mmol) in THF (30 mL) was added to lithium foil (~100 mg) at room temperature and the mixture was stirred for 3 hr. An orange solution formed. The solution was separated from the excess of lithium and was treated with a THF solution (20 mL) of Me$_3$SnCl (0.696 g, 3.50 mmol) at −100° C. A colorless solution formed. The solution was warmed up to 23° C. and pumped to dryness. The residue was redissolved in toluene (10 mL) and the slurry pumped to dryness to remove trace amounts of THF. Toluene (10 mL) was added to the flask again to dissolve the residue and the slurry was filtered into a slurry of ZrCl4 (0.659 g, 1.747 mmol) in toluene (10 mL). A reddish orange solution formed after the addition. The solution was warmed to 100° C. for 3 hr and then pumped to dryness. The product was isolated by recrystallization of the residue from ether. $^1$H NMR (C$_7$D$_8$, d): 0.827(s, 3H), 0.907 (d, J=0.95 Hz, 3H), 1.848 (s, 3H), 1.988 (s, 3H), 6.67 (d, J=38 Hz, 1H), 7.1–7.9 (m, 8H).

PART A5

Synthesis of 2-dimethyl(2,7-di-tert-butyl-9-fluorenyl)silyl-3,4,5-trimethyl-1-phenylphosphole

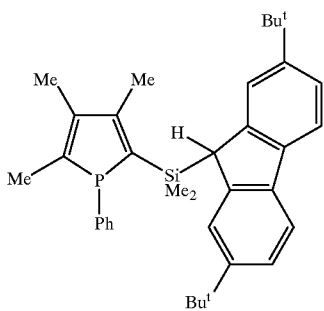

Step 1. 2,7-di-tert-butyl-fluorenyl lithium (1.6 mmol) was prepared by reacting 2,7-di-tert-butyl-fluorene (1.6 mmol, 0.445) and "BuLi (1.6 mol) in diethyl ether at 23° C. for 2 hours.

Step 2. The title compound was prepared by reacting 2,7-di-tert-butyl-fluorenyl lithium (1.6 mmol, from Step 1 above) with 2-chlorodimethylsilyl-1-phenyl-3,4,5 trimethylphosphole (1.6 mmol, 0.472 g) using the procedures previously described in Parts A1 and A4. 1H NMR (C$_7$D$_8$): −0.30(br. s), 0.38 (br. s), 1.36(s), 1.37 (s), 1.90(d), 1.94 (d), 2.03 (d), 3.96 (s), 6.9–7.8 (m).

PART B

Solution Polymerization

Part B illustrates the (co)-polymerization of ethylene under solution polymerization conditions. Part B1 describes continuous flow solution polymerizations. Part B2 describes batch solution polymerizations. Inventive polymerizations using "bridged phospholes" are polymerizations done with prior art, unbridged phospholes and to metallocenes. The data clearly illustrate that the inventive systems provide excellent polymerization rates. In addition, the dimethyl silyl bridged phosphole-fluorenyl complexes provide high molecular weight polymers under high temperature polymerization conditions.

PART B1

Continuous Solution Polymerization

All the polymerization experiments described below were conducted on a continuous solution polymerization reactor. The process is continuous in all feed streams (solvent, monomers and catalyst) and in the removal of product. All feed streams were purified prior to the reactor by contact with various absorption media. All components were stored and manipulated under an atmosphere of purified nitrogen.

All the examples below were conducted in a reactor of 71.5 cubic centimeters (cc) internal volume. In each experiment the volumetric feed to the reactor was kept constant and as a consequence so was the reactor residence time.

The catalyst solutions were pumped to the reactor independently and there was no pre-contact between the activator and the catalyst. Because of the low solubility of the catalyst and the MAO in cyclohexane, solutions were prepared in toluene. The catalyst was activated in situ (in the polymerization reactor) at the reaction temperature in the presence of the monomers. The polymerizations were carried out in cyclohexane at a pressure of 1500 pounds per square inch (psi). Ethylene was supplied to the reactor by a calibrated thermal mass flow meter and was dissolved in the reaction solvent prior to the polymerization reactor. If comonomer was used it was also premixed with the ethylene before entering the polymerization reactor. Under these conditions the ethylene conversion is a dependent variable controlled by the catalyst concentration, reaction temperature and catalyst activity etc.

The internal reactor temperature is monitored by a thermocouple in the polymerization medium and can be controlled at the required set point to ±0.5° C. Downstream of the reactor the pressure was reduced from the reaction pressure (1500 psi) to atmospheric. The solid polymer was then recovered as a slurry in the condensed solvent and was dried by evaporation before analysis.

The ethylene conversion was determined by a dedicated on line gas chromatograph.

Polymer Analysis

Gel permeation chromatography ("GPC") analysis was carried out on a Waters 150C GPC using 1,2,4-trichlorobenzene as the mobile phase at 140° C. The samples were prepared by dissolving the polymer in the mobile phase solvent in an external oven at 0.1% (weight/volume) and were run without filtration. Molecular weights are expressed as polyethylene equivalents with a relative standard deviation of 2.9% and 5.0% for the number average molecular weight (Mn) and weight average molecular weight (Mw), respectively.

Melt index (MI) measurements were conducted according to ASTM method D-1238-82.

Polymer densities were measured on pressed plaques (ASTM D-1928-90) with a densitometer.

Example B1

Me$_2$Si(Cp)(C$_4$PMe$_3$)ZrCl$_2$ was added to the reactor at 37×10$^{-6}$ mol/l along with PMAO-IP (Akzo-Nobel) at Al/Ti= 200 (mol/mol). The reaction temperature was 160° C. and 1 gram/min (g/min) of ethylene was continuously added to the reactor. An ethylene conversion of 86.4% was observed (see table 1).

Example B2

Conditions were as in example B1 except that 2.1 g/min of ethylene was added to the reactor. An ethylene conversion of 87.9% was seen (see table 1).

Example B3

Conditions were as in example B1 except that 2.1 g/min of ethylene and 3 ml/min of 1-octene was added to the reactor. An ethylene conversion of 87.2% was seen (see table 1).

Comparative Example B4-C

This comparative example uses an unbridged cyclopentadienyl-phospholyl complex. Thus, ($\eta^5$-cyclopentadienyl)($\eta^5$-2,3,4,5-tetramethylphospholyl) zirconium dichloride ("(Cp)($C_4PMe_4$)$ZrCl_2$") was added to the reactor at $37\times10^{-6}$ mol/l along with MMAO-3 (Akzo-Nobel) at Al/Ti=400 (mol/mol). The reaction temperature was 160° C. and 1 gram/min of ethylene was continuously added to the reactor. An ethylene conversion of 68.3% was observed (see table 2).

Comparative Example B5-C

This comparative example also uses the unbridged complex (Cp)($C_4PMe_4$)$ZrCl_2$. Thus, (Cp)($C_4PMe_4$)$ZrCl_2$ was added to the reactor at $37\times10^{-6}$ mol/l along with MMAO-3 (Akzo-Nobel) at Al/Ti=400 (mol/mol). The reaction temperature was 160° C. and 2.1 gram/min of ethylene was continuously added to the reactor. An ethylene conversion of 79.3% was observed (see table 2).

Comparative Example B6-C (Cp)($C_4PMe_4$)$ZrCl_2$ was added to the reactor at $37\times10^{-6}$ mol/l along with MMAO-3 (Akzo-Nobel) at Al/Ti=400 (mol/mol). The reaction temperature was 160° C. and 2.1 gram/min of ethylene and 3.25 ml/min of 1-octene was continuously added to the reactor. An ethylene conversion of 81.0% was observed (see table 2).

Comparative Example B7-C

This comparative example employs a metallocene catalyst (i.e. no phospholyl ligand). Thus, ($C_5Me_5$)$_2$$ZrCl_2$ was added to the reactor at $37\times10^{-6}$ mol/l along with MMAO-3 (Akzo-Nobel) at Al/Ti=400 (mol/mol). The reaction temperature was 160° C. and 1 gram/min of ethylene was continuously added to the reactor. An ethylene conversion of 35.6% was observed (see table 2).

Comparative Example B8-C ($C_5Me_5$)$_2$$ZrCl_2$ was added to the reactor at $37\times10^{-6}$ mol/l along with MMAO-3 (Akzo-Nobel) at Al/Ti=400 (mol/mol). The reaction temperature was 160° C. and 2.1 gram/min of ethylene was continuously added to the reactor. An ethylene conversion of 37.4% was observed (see table 2).

Comparative Example B9-C ($C_5Me_5$)$_2$$ZrCl_2$ was added to the reactor at $37\times10^{-6}$ mol/l along with MMAO-3 (Akzo-Nobel) at Al/Ti=400 (mol/mol). The reaction temperature was 160° C. and 2.1 gram/min of ethylene and 3.25 ml/min of 1-octene was continuously added to the reactor. An ethylene conversion of 38.5% was observed (see table 2).

Comparative Example B10-C ($C_4PMe_4$)$_2$$ZrCl_2$ was added to the reactor at $37\times10^{-6}$ mol/l along with MMAO-3 (Akzo-Nobel) at Al/Ti=400 (mol/mol). The reaction temperature was 160° C. and 1 gram/min of ethylene was continuously added to the reactor. An ethylene conversion of 36.6% was observed (see table 2).

TABLE 1

| Example | Total Flow To Reactor (ml/min) | Catalyst Concentration (mol $\times$ $10^6$) | Ethylene Conversion (%) | Calculated Polymerization Rate (l/mmol $\times$ min) | Polymer Density (g/cc) | Polymer Melt Index |
|---|---|---|---|---|---|---|
| B1 | 27.0 | 37.0 | 86.4 | 64.9 | — | — |
| B2 | 27.0 | 37.0 | 73.8 | 73.8 | >0.94 | 1400 |
| B3 | 27.0 | 37.0 | 87.2 | 69.7 | >0.94 | 2000 |

TABLE 2

(Comparative Examples)

| Example | Total Flow To Reactor (ml/min) | Catalyst Concentration (mol $\times$ $10^6$) | Ethylene Conversion (%) | Calculated Polymerization Rate (l/mmol $\times$ min) | Polymer Mn $\times$ $10^{-3}$ | Polymer Mw $\times$ $10^{-3}$ | Polymer Density (g/cc) | Polymer Melt index |
|---|---|---|---|---|---|---|---|---|
| B4-C | 27.0 | 37.0 | 68.3 | 22.0 | 7.8 | 21 | — | — |
| B5-C | 27.0 | 37.0 | 79.3 | 39.1 | 7.0 | 23.8 | — | 155 |
| B6-C | 27.0 | 37.0 | 81.0 | 43.5 | 6.7 | 19 | 0.923 | — |
| B7-C | 27.0 | 37.0 | 35.6 | 5.6 | 1.8 | 7.5 | — | — |
| B8-C | 27.0 | 37.0 | 37.4 | 6.1 | 3.3 | 12 | 0.987 | 620 |
| B9-C | 27.0 | 37.0 | 38.5 | 6.4 | 1.9 | 9.3 | — | — |
| B10-C | 27.0 | 37.0 | 36.6 | 5.9 | 3.5 | 14.3 | — | — |

PART B2

Solution Batch Reactor Polymerizations

Anhydrous toluene was purchased from Aldrich and used without further purification. The catalysts $Me_2Si(Flu)$($C_4PMe_3$)$ZrCl_2$ (1) and $Me_2Si(Flu)$($C_4PHMe_2$)$ZrCl_2$ (2) used in this study were synthesized as described in Part A above and were used without further purification. Catalyst 1 was dissolved in toluene at 50° C. with the help of an ultrasound bath. Catalyst 2 was dissolved in toluene at room temperature. The catalyst concentrations were between 6–7 mg/mL. A portion of this solution was then injected into the reactor to give the required reactor catalyst concentration. A comparative experiment was also completed with a known metallocene having a dimethyl silyl bridge between a cyclopentadienyl group and a fluorenyl group.

A solution semi-batch reactor (SBR) was used in the polymerization experiments. The SBR uses a programmable logical control (PLC) system with commercially available software (Wonderware 5.1) for process control. Ethylene (99.5%, polymer grade, Matheson) and cyclohexane was purified by absorption before use. MAO (MMAO-3 or PMAO-IP) was purchased from Akzo-Nobel. Ethylene polymerizations were performed in a 500 mL Autoclave Engineers Zipperclave reactor equipped with an air driven stirrer and an automatic temperature control system. The experiments were carried out as follows:

| | |
|---|---|
| Cyclohexane | 228 mL |
| Catalyst Concentration | 53 or 65 µmol/L |
| Cocatalyst | MAO (MMAO-3 or PMAO-IP; Al/Zr = 300 or 400 mol/mol) |
| Reaction Temperature | 160° C. |
| Reactor Pressure | 140 psig total |
| Stirring Speed | 2000 rpm |

The polymerization time was 10 min in each experiment. The reaction was terminated by adding 5 mL of methanol to the reactor and the polymer was recovered by evaporation of the cyclohexane.

Polymer molecular weights and molecular weight distributions were measured by GPC (Waters 150-C) at 140° C. in 1,2,4-trichlorobenzene calibrated using polyethylene standards.

Example C1

Use of $Me_2Si(Cp)(C_4PMe_3)ZrCl_2$

Preparation of Supported Catalyst

Commercial MAO on granular silica (1.23 g, Witco TA 02794/HL/04, 23 wt % Al) was suspended in anhydrous toluene (40 mL). A solution of $Me_2Si(Cp)(C_4PMe_3)ZrCl_2$ was prepared in anhydrous toluene (0.012 mol/L) and a volume of 10 mL of this solution was added dropwise to a stirred suspension of the MAO on silica. The mixture was allowed to stir overnight and subsequently heated at 45° C. for a period of 2.5 hours. The resulting solid was collected via filtration and washed first with toluene (2×15 mL) and then hexane (2×20 mL). After drying in vacuo, 1.13 grams of a free-flowing powder was obtained.

Polymerization

Gas phase ethylene homopolymerization of the supported catalyst was conducted by introducing the catalyst (23 mg) into a continuously stirred, 2L pressure vessel under operating conditions of 200 psig ethylene (Praxair, polymerization grade) and at a constant temperature of 90° C. for a period of 1 hr. A seed bed of NaCl (70 g, oven dried at 175° C. for 48 hours), treated in situ with a heptane solution of tri-isobutylaluminum (TIBAI, 1 mL of a 25 wt % solution, Akzo Nobel), was added to the reactor prior to introduction of the catalyst. Upon termination of the reaction and isolation of the polymer, a free-flowing product was obtained in a yield of 41 g, representing a catalyst activity of 198,000 g PE/g Zr×hr. The polymer, characterized by gel permeation chromatography (GPC), showed a molecular weight of 89,000 (Mw) and a polydispersity of 2.2.

TABLE 1A (Polymerization Activity)

| Example | Catalyst | Cocatalyst | Al/Zr (mol/mol) | Catalyst Concentration | Polymerization Activity g PE/m Molcat*hr[1] |
|---|---|---|---|---|---|
| B11 | $Me_2Si(Flu)(C_4PMe_3)ZrCl_2$ | PMAO-IP | 300 | 53 µmol/L | 2883.1 |
| B12 | $Me_2Si(Flu)(C_4PHMe_2)ZrCl_2$ | PMAO-IP | 300 | 65 µmol/L | 2219.4 |
| B13-C | $SiPh_2CpFluZrCl_2$ | MMAO-3 | 400 | 65 µmol/L | 1148.8 |

[1] The calculation of polymerization activity is based on the ethylene uptake.

TABLE 2A (Polymer Properties)

| Example | Catalyst | Cocatalyst | Al/Zr (mol/mol) | Catalyst Concentration | Mw(*10⁻³) | Mw/Mn |
|---|---|---|---|---|---|---|
| B11 | $Me_2Si(Flu)(C_4PMe_3)ZrCl_2$ | PMAO-IP | 300 | 53 µmol/L | 73 | 4.2 |
| B12 | $Me_2Si(Flu)(C_4PHMe_2)ZrCl_2$ | PMAO-IP | 300 | 65 µmol/L | 37 | 3.0 |
| B13-C | $SiPh_2CpFluZrCl_2$ | MMAO-3 | 400 | 65 µmol/L | 21 | 2.3 |

The inventive experiments using the "bridged fluorenyl phosphole" complexes (i.e. examples B11 and B12) are different from the comparative experiment using the "bridged fluorenyl cyclopentadienyl" complex in the following respects:
(a) the inventive polymerizations were more active;
(b) the polymers produced by the inventive experiments have higher molecular weight (which is very desirable for high temperature polymerizations); and
(c) the polymer from the comparative experiment has a narrower molecular weight distribution.

PART C

Gas Phase Polymerization

This section illustrates gas phase polymerization according to the present invention and also provides comparative examples.

Example C2

Ethylene-1-butene Copolymerization using Silica Supported $Me_2Si(Cp)(C_4PMe_3)ZrCl_2$ Polymerization Gas phase ethylene-1-butene copolymerization of the supported catalyst described in Example C1 was conducted by introducing the catalyst (23 mg) into a continuously stirred, 2L pressure vessel under operating conditions of 200 psig of a continuously supplied four mol % mixture of 1-butene in ethylene (Airgas, polymerization grade) and at a constant temperature of 90° C. for a period of 1 hr. A seed bed of NaCl (70 g, oven dried at 175° C. for 48 hours), treated in situ with a heptane solution of tri-isobutylaluminum (TIBAI, 1 mL of a 25 wt % solution, Akzo Nobel), was added to the reactor prior to introduction of the catalyst. Upon termination of the reaction and isolation of the polymer, a free-flowing product was obtained in a yield of 39 g, representing a catalyst productivity of 185,000 g PE/g Zr×hr. The polymer, characterized by gel permeation chromatography (GPC), showed a molecular weight of 111,000 (Mw) and a polydispersity of 3.5.

Example C3

Ethylene Polymerization using Silica Supported $Me_2Si(Flu)(C_4PMe_3)ZrCl_2$

Catalyst Synthesis

Commercial MAO on granular silica (0.45 g, Witco TA 02794/HL/04, 23 wt % Al) was suspended in anhydrous toluene (10 mL). A solution of $Me_2Si(Flu)(C_4PMe_3)ZrCl_2$ was prepared in anhydrous toluene (0.00064 mol/L) and a volume of 69 mL of this solution was added dropwise to a stirred suspension of the MAO on silica. The mixture was allowed to stir overnight. The resulting solid was collected via filtration and washed first with toluene (2×15 mL) and then hexane (2×20 mL). After drying in vacuo for 1 hour, a free-flowing powder was obtained.

Polymerization

Gas phase ethylene homopolymerization of the supported catalyst was conducted by introducing the catalyst (18 mg) into a continuously stirred, 2L pressure vessel under operating conditions of 200 psig ethylene (Praxair, polymerization grade) and at a constant temperature of 90° C. for a period of 1 hr. A seed bed of NaCl (70 g, oven dried at 175° C. for 48 hours), treated in situ with a heptane solution of tri-isobutylaluminum (TIBAI, 1 mL of a 25 wt % solution, Akzo Nobel), was added to the reactor prior to introduction of the catalyst. Upon termination of the reaction and isolation of the polymer, a free-flowing product was obtained in a yield of 15 g, representing a catalyst productivity of 97,000 g PE/g Zr×hr.

Comparative Example C4-C

Preparation and Ethylene Polymerization of Silica Supported Bis-tetramethylphospholyl Zirconium Dichloride Catalyst Preparation The same procedure as described in Example C1 was used, except that an unbridged bis phospholyl, namely bis-tetramethylphospholyl zirconium dichloride (25 mL having a concentration of 0.016 mol/L), was used. 1.7 g of catalyst was obtained.

Polymerization

Using the same procedure as described in Example C1, 4.7 g of polyethylene was obtained, representing a catalyst productivity of 20,600 g/g Zr×hr. The polymer, characterized by gel permeation chromatography (GPC), showed a molecular weight of 226,000 (Mw) and a polydispersity of 4.9.

Comparative Example C2-C

Preparation and Ethylene Polymerization of Silica Supported Tetramethylphospholyl(cyclopentadienyl) Zirconium-dichloride Catalyst Preparation The same procedure as described in Example C1 was used, except that Tetramethylphospholyl(cyclopentadienyl) zirconium dichloride (35 mL having a concentration of 0.017 mol/L) was used. 2.8 g of the MAO on silica was used. 2.7 g of catalyst was obtained.

Polymerization

Using the same procedure as described in Example C1, 4.8 g of polyethylene was obtained, representing a catalyst productivity of 20,800 g/g Zr×hr. The polymer, characterized by gel permeation chromatography (GPC), showed a molecular weight of 209,000 (Mw) and a polydispersity of 6.9.

What is claimed is:

1. A process for polymerizing at least one polymerizable alpha olefin comprising reacting a cocatalyst and a group 4 organometallic complex with said at least one alpha olefin, wherein said group 4 organometallic complex is defined by the formula:

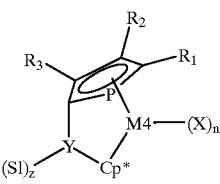

2. The process according to claim 1 wherein said cocatalyst is an alumoxane.

3. The process according to claim 1 wherein said cocatalyst is an ionic activator.

4. The process according to claim 1 wherein said at least one polymerizable alpha olefin comprises a majority of ethylene and a minor portion of at least one of propylene, butene-1, pentene-1, hexene-1, and octene-1.

5. The process according to claim 1 when conducted in a gas phase polymerization reactor.

6. A process for the polymerization of at least one olefin comprising reacting at least one alpha olefin monomer under polymerization conditions with a cocatalyst and a group 4 organometallic complex of the formula:

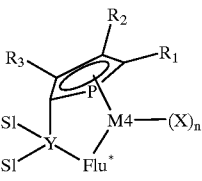

wherein:

Flu* is selected from fluorenyl and substituted fluorenyl;

each Sl is a non-interfering spectator ligand;

Y is selected from Si, Ge, and Sn;

$R_1$, $R_2$, and $R_3$ are hydrogen or non-interfering substituents;

M4 is selected from Ti, Zr and Hf;

X is an anionic ligand; and n is 1 or 2 depending upon the oxidation sate of M4.

7. The process according to claim 6 wherein said cocatalyst is an ionic activator.

8. The process according to claim 6 wherein said at least one alpha olefin comprises a majority of ethylene and a minor portion of at least one of propylene, butene-1, pentene-1, hexene-1 and octene-1.

9. The process according to claim 6 when conducted at a temperature of from 120° C. to 300° C.

10. The process according to claim 6 when conducted in the presence of a solvent for the polymer produced by the process.

11. A medium pressure solution polymerization process comprising reacting an activator and a group 4 metal complex having a bridged fluorenyl phospholyl ligand with at least one polymerizable alpha olefin at a temperature of from 140° C. to 300° C. at a pressure of from 4 to 20 mega Pascals in a solvent for polymer produced by the process.

12. The process according to claim 11 wherein said cocatalyst is an ionic activator.

13. The process according to claim 12 wherein said ionic activator is provided as a carbonium salt of a substantially non-coordinating anion.

14. The process according to claim 11 wherein said group 4 metal complex is defined by the formula:

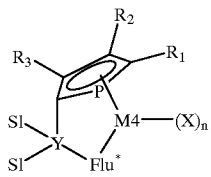

wherein:
Flu* is selected from fluorenyl and substituted fluorenyl;
each Sl is a non-interfering spectator ligand;
Y is selected from Si, Ge, and Sn;
$R_1$, $R_2$, and $R_3$ are hydrogen or non-interfering substituents;
M4 is selected from Ti, Zr and Hf;
X is an anionic ligand; and
n is 1 or 2 depending upon the oxidation sate of M4.

* * * * *

UNITED STATES PATENT AND TRADEMARK OFFICE
CERTIFICATE OF CORRECTION

PATENT NO : 6,051,667
DATED : 04/18/00
INVENTOR(S): Spence et al.

It is certified that error appears in the above-identified patent and that said Letters Patent is hereby corrected as shown below: Title page, item [75], inventors:

The last name of the first named inventor is Spence, not Von Haken Spence.

Signed and Sealed this

Twenty-seventh Day of February, 2001

Attest:

NICHOLAS P. GODICI

Attesting Officer

Acting Director of the United States Patent and Trademark Office